US00PP09880P

United States Patent [19]

Hayashi

[11] Patent Number: Plant 9,880

[45] Date of Patent: Apr. 29, 1997

[54] ANTHURIUM PLANT NAMED JASMINE

[76] Inventor: Calvin K. Hayashi, P.O. Box 242, Pahoa, Hi. 96778

[21] Appl. No.: 567,744

[22] Filed: Dec. 5, 1995

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—Banner & Witcoff, Ltd.

[57] ABSTRACT

Jasmine, a cultivar of *Anthurium andraeanum*, is the product of a cross between Starlight and Midori. Jasmine has yellow-green, generally heart-shaped spathe with an indentation.

2 Drawing Sheets

The present invention comprises a new and distinct cultivar of Anthurium, botanically known as *Anthurium adnraeanum*, and hereinafter referred to by the cultivar name Jasmine. This new cultivar is a product of a planned breeding program, and was created from a cross made during such a program in Pahoa, Hi., U.S.A. The female, or seed parent was Starlight and the male, or pollen plant, was Midori. Jasmine was discovered and selected as a flowering plant within the progeny of the stated cross by Calvin K. Hayashi in a controlled growing environment in Pahoa, HI., U.S.A. Subsequent asexual reproduction has demonstrated that the combination of characteristics as herein disclosed for the new cultivar are firmly fixed and are retained through successive generations of asexual reproduction.

SUMMARY OF THE INVENTION

The following traits have been repeatedly observed and in combination distinguish Jasmine as a new and distinct cultivar:

The spathe or blossoms are a light yellow-green with a length of 8 inches and a width of 6½ inches.

The shape of the spathe is generally heart-shaped with one edge slightly indented.

The pedicle is straight and strong, and the spathe stand well above the leaves.

The leaves are relatively large, and dark green in color. New leaves grow approximately 40 inches in overall height when grown to maturity in a 10 inch plastic container.

The spadix is approximately 4½ inches long, 1⅞ inches in circumference, having a generally yellow-green color at early growth stages and maturing into an ivory color at maturity.

The plant flowers continuously. When first flowering, the spathe are small in size, becoming larger with each successive blossom as the plant matures in growth.

BRIEF DESCRIPTION OF THE DRAWINGS

The accompanying photographs show a typical specimen of the new cultivar Jasmine, with the colors being as true as possible with illustrations of this type.

DETAILED DESCRIPTION OF THE PREFERRED EMBODIMENTS

Figure 1:
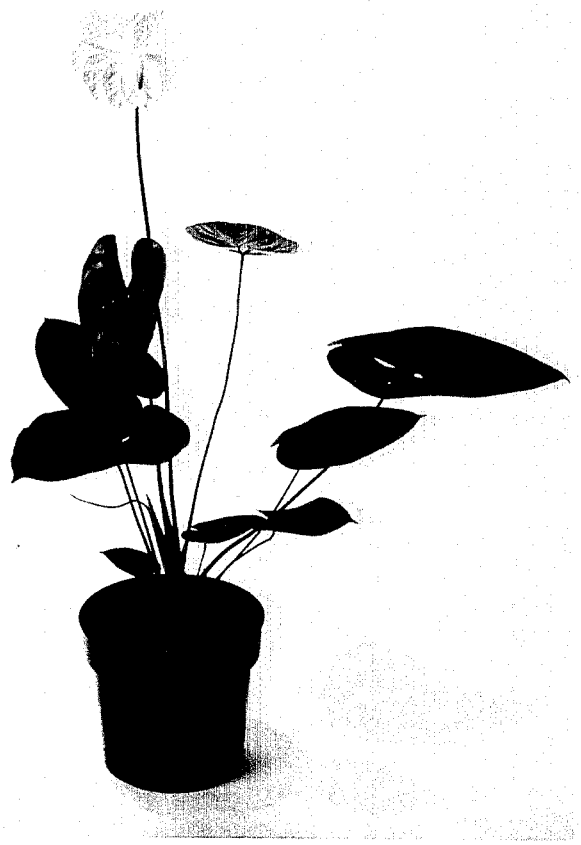
FIG. 1 is a frontal perspective view of the entire plant.
Figure 2:
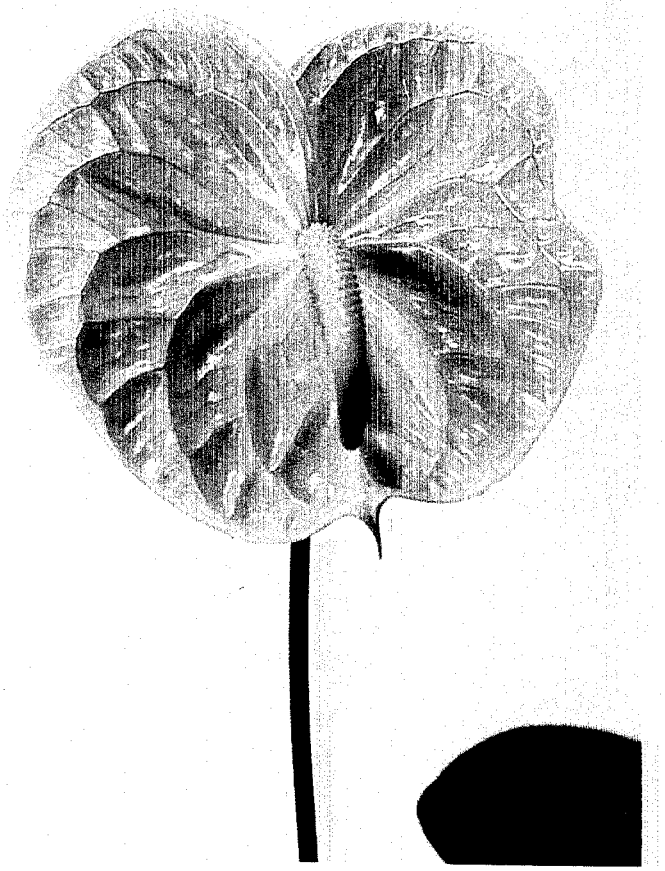
FIG. 2 is a close up view of a typical spathe.

The following observations, measurements, and values describe the plant grown in Pahoa, Hi., U.S.A., under greenhouse conditions which closely approximate those generally used in horticultural practice. Color references are made to The R.H.S. Colour Chart of The Royal Horticultural Society, except where general color terms of ordinary significance are used.

Botanical classification: *Anthurium andraeanum*, cultivar name, Jasmine.

Parentage:

*Male parent.*—*Anthurium andraeanum* Midori.

*Female parent.*—*Anthurium andraeanum* Starlight.

Propagation: At the present time, propagation is by stem cutting although tissue culture is possible with this cultivar.

Plant: When grown in a 10-inch plastic container the plant is approximately 40 inches in height and approximately 38 inches in width.

Leaves:

*Form and size.*—The leaves are generally heart-shaped, with a distinct point. The size of the leaves, depending on the maturity of the plant, is approximately 14½ inches to 8½ inches in width.

*Texture.*—Smooth, slightly shiny in appearance.

*Color.*—Upper side dark green; under side medium green, stems are a light green than the leaves.

Flowers:

*Buds.*—The spathe is rolled around the spadix; after opening, the spathe stands well above the leaves.

Spathe (blossom):

*Size.*—Approximately 8 inches in length and 6½ inches in width.

*Color.*—Upperside, 150D; underside, 150D. The color designation is primarily yellow-green with a light green coloration along the veins.

*Arrangement.*—The spathe stand on long, straight light green pedicles and are set at an angle approximately 45 degrees to the pedicle.

*Shape.*—At full bloom, the spathe is generally heart-shaped with the lobes slightly overlapping. The veins begin at the base of the spadix and are visible throughout the spathe. The edge of the spathe is slightly indented on one side.

*Texture.*—Glossy.

Reproductive organs:

*Spadix.*—Generally yellow-green in color maturing to an ivory white.

*Stamens.*—There are four stamens surrounding the pistil. The stamens are visible only when they are separated from the individual reproductive organs from the main axil. The stamens are covered with two small triangular and two square-shaped tops; at the center, the stamen is firmly enclosed.

*Anthers and filaments.*—Not clearly visible.

*Pollen.*—White in color.

*Pistils.*—Grown firmly together with the pulpy main axil and sitting between the stamens. The color is generally yellow, maturing to an ivory white and shaped approximately 1/16 of an inch long.

Roots: New growth is pulpy and light red in color, with the very tips being yellow. Older roots are generally gray.

Disease resistance: Through observation to date, Jasmine exhibits good tolerance against traditional diseases.

General observations: Jasmine is a rapid growing anthurium which under optimum growing conditions produces approximately six blossoms per year. At earlier stages of growth, the plant produces smaller blooms which become larger as the plant matures. The spathe are held on long, straight pedicles reaching lengths of 34 inches. This new and distinct cultivar, because of its good blooming habit and coloration is well suited for cut flower production as well as for potted plants. Due to this unique combination of characteristics, Jasmine provides a valuable new cultivar of *Anthurium adraeanum.*

I claim:

1. A new and distinct cultivar of *Anthurium andraeanum* substantially as described and illustrated, known by the cultivar name Jasmine and characterized by the combined features of a yellow-green, generally heart-shaped spathe and an indentation along an edge thereof; long straight pedicles which hold and position the spathe well above the leaves; dark green leaves; slightly spreading growth habit and good blooming habit.

* * * * *